US009346916B2

(12) United States Patent
Wang et al.

(10) Patent No.: US 9,346,916 B2
(45) Date of Patent: May 24, 2016

(54) FLUIDIZED BED REACTOR AND METHOD FOR PREPARING POLYOXYMETHYLENE DIMETHYL ETHERS FROM DIMETHOXYMETHANE AND PARAFORMALDEHYDE

(71) Applicants: Shandong Yuhuang Chemical Co., Ltd., Shandong Province (CN); Tsinghua University, Beijing (CN)

(72) Inventors: Jinfu Wang, Beijing (CN); Qiang Tang, Beijing (CN); Shengwei Wang, Shandong Province (CN); Tiefeng Wang, Beijing (CN); Shuangxi Chen, Shandong Province (CN); Yuqiang Wang, Shandong Province (CN)

(73) Assignees: SHANDONG YUHUANG CHEMICAL CO., LTD., Shandong Province (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 14/589,651

(22) Filed: Jan. 5, 2015

(65) Prior Publication Data

US 2015/0273426 A1    Oct. 1, 2015

(30) Foreign Application Priority Data

Apr. 1, 2014    (CN) .......................... 2014 1 0128524

(51) Int. Cl.
*B01J 8/24*    (2006.01)
*B01J 8/28*    (2006.01)
(Continued)

(52) U.S. Cl.
CPC ............... *C08G 65/00* (2013.01); *B01J 8/1818* (2013.01); *B01J 8/1827* (2013.01); *B01J 8/1836* (2013.01);
(Continued)

(58) Field of Classification Search
None
See application file for complete search history.

(56) References Cited

U.S. PATENT DOCUMENTS 4,457,896 A * 7/1984 Kono .................. B01J 8/28
                                                  208/164

(Continued)

FOREIGN PATENT DOCUMENTS

CN    101195554 A    6/2008
CN    101274879 A    10/2008
(Continued)

OTHER PUBLICATIONS

International Search Report and Written Opinion regarding Application No. PCT/CN2015/075078, dated Jun. 26, 2015. English-language translation is not available.

*Primary Examiner* — Rosalynd Keys
(74) *Attorney, Agent, or Firm* — Stephen T. Olson; Harness, Dickey & Pierce, P.L.C.

(57) ABSTRACT

The invention belongs to energy chemical technical field, especially relates to a fluidized bed reactor and a method for preparation of polyoxymethylene dimethyl ethers from dimethoxymethane and paraformaldehyde. The fluidized bed reactor comprises a gas inlet, a gas distributor, a catalyst inlet, a gas outlet, a fluid inlet, a catalyst outlet, a bottom component and an interstage component, a bottom component related gas upward channel, an interstage component related gas upward channel, a fluid outlet, a bottom downcomer and an interstage downcomer. A process for preparation of polyoxymethylene dimethyl ethers comprises the steps of: fluidizing gas is introduced into a bottom bed from the gas inlet via the bottom component related gas upward channel through the gas distributor; the fluidizing gas goes upwards and flows out of the reactor via the gas outlet; paraformaldehyde and dimethoxymethane are introduced into a bed through the fluid inlet; the fluid goes downwards and leaves the reactor via the fluid outlet. Compared with a conventional cannula reactor, the fluidized bed reactor improves the dispersion uniformity of catalyst and conversion of formaldehyde.

13 Claims, 3 Drawing Sheets

(51) Int. Cl.
   *C08G 65/00* (2006.01)
   *B01J 8/18* (2006.01)

(52) U.S. Cl.
   CPC ............ *B01J 8/28* (2013.01); *B01J 2208/0092* (2013.01); *B01J 2208/00212* (2013.01); *B01J 2208/00902* (2013.01); *B01J 2208/00911* (2013.01)

(56) References Cited

U.S. PATENT DOCUMENTS

| | | |
|---|---|---|
| 5,959,156 A | 9/1999 | Hagan et al. |
| 6,160,174 A | 12/2000 | Hagen et al. |
| 6,160,186 A | 12/2000 | Hagen et al. |
| 6,392,102 B1 | 5/2002 | Hagen et al. |
| 7,560,599 B2 | 7/2009 | Chen et al. |
| 7,671,240 B2 | 3/2010 | Stroefer et al. |
| 7,700,809 B2 | 4/2010 | Stroefer et al. |
| 2007/0260094 A1 | 11/2007 | Schelling et al. |
| 2010/0056830 A1 | 3/2010 | Chen et al. |
| 2011/0288343 A1 | 11/2011 | Chen et al. |

FOREIGN PATENT DOCUMENTS

| | | | |
|---|---|---|---|
| CN | 201768553 | * 3/2011 | ................ B01J 8/24 |
| CN | 201768553 U | 3/2011 | |
| CN | 102249869 A | 11/2011 | |
| CN | 102701923 A | 10/2012 | |
| CN | 104292085 A | 1/2015 | |

* cited by examiner

FLUIDIZED BED REACTOR AND METHOD FOR PREPARING POLYOXYMETHYLENE DIMETHYL ETHERS FROM DIMETHOXYMETHANE AND PARAFORMALDEHYDE

CROSS REFERENCE TO RELATED APPLICATIONS

The present application is based on, and claims priority from, Chinese application number 201410128524.9, filed on Apr. 1, 2014, the disclosure of which is hereby incorporated by reference herein in its entirety

FIELD OF THE INVENTION

The invention relates to a fluidized bed reactor and a method for preparing polyoxymethylene dimethyl ethers from dimethoxymethane and paraformaldehyde.

TECHNICAL BACKGROUND

Diesel is an essential power fuel for engine and machine. In China, diesel frequently encounters supply crisis due to large market demand and serious lacking of petroleum. At the same time, consumption of diesel not only leads to serious environmental pollution such as haze, but also makes a threat to the health of human beings. A green diesel additive could significantly improve the combustion efficiency of diesel, and decrease exhaust (such as particular matter, $NO_x$ and CO etc) emission. Therefore, research and development of green diesel additive is of great importance.

Polyoxymethylene dimethyl ethers have received global attention as a potential green diesel additive. Polyoxymethylene dimethyl ethers refer to a series of homologue compounds $CH_3O(CH_2O)_nCH_3$, denoted by $PODE_n$. $PODE_{3-5}$ showed oxygen content (~50%) and cetane number (70~100). The fuel properties of $PODE_{3-5}$ are close to that of diesel. Addition of $PODE_{3-5}$ into diesel could significantly improve the combustion efficiency of diesel, and decrease exhaust (such as particular matter, $NO_x$ and CO etc) emission, thus upgrading the environmental and economic benefits.

Recently, many companies and research institutes are developing the production process of polyoxymethylene dimethyl ethers. Nevertheless, there has been no industrialized plant yet.

U.S. Pat. No. 5,959,156A, U.S. Pat. No. 6,160,174A, U.S. Pat. No. 6,160,186A, U.S. Pat. No. 6,392,102B1 by British Petroleum (BP) describe a process in which methanol or dimethyl ether is converted to formaldehyde via oxidative dehydrogenation, and then formaldehyde reacts with methanol or dimethyl ether forming dimethoxymethane and polyoxymethylene dimethyl ethers. The process is very complex, comprising unit operations including oxidative dehydrogenation, adsorption cooling, catalytic distillation, neutralization and separation. The selectivity to $PODE_{n>1}$ in polyoxymethylene dimethyl ethers is less than 10%.

U.S. Pat. No. 7,700,809B2, US 20070260094A1, U.S. Pat. No. 7,671,240B2 by BASF describe the preparation of polyoxymethylene dimethyl ethers from dimethoxymethane and trioxane in the presence of acidic catalyst. The selectivity to $PODE_{3-5}$ in polyoxymethylene dimethyl ethers is about 20 wt %, owing to the low water content in system (<1%). However, the cost of highly purified troxane and dimethoxymethane is too high. Besides, a considerable amount of by-products PODEn>5 are produced, thus complicating the separation process.

U.S. Pat. No. 0,056,830A1, U.S. Pat. No. 7,560,599B2 by Lanzhou Institute of Chemical Physics, Chinese Academy of Sciences, describe the preparation of polyoxymethylene dimethyl ethers from methanol and trioxane in the presence of acidic ionic liquid. The conversion of trioxane could reach 90%. However, ionic liquid is unfavorable due to high cost, difficult separation and recycling, thus complicating the process.

In production process of polyoxymethylene dimethyl ethers, reactor is the most important operation unit. Design of reactor would determine conversion of formaldehyde, selectivity to target products, production continuity and processing capacity. The published patents mainly focus on the technological process and catalyst, but rarely on the reactor design. Besides, feedstock cost is too high when using trioxane as source of formaldehyde, which seriously affect the economic benefits.

In bench-scale studies on preparation of polyoxymethylene dimethyl ethers, batch reactors are mostly used. It is unfavorable to be directly scaled-up due to low processing capacity and long production period. CN102249869A describes a cannula reactor for preparation of polyoxymethylene dimethyl ethers from methanol and trioxane in the presence of ionic liquid. However, this reactor has disadvantages including unstable system temperature, undermixing of reactants, nonuniform dispersion of catalyst, low conversion of reactants, high cost of trioxane and ionic liquid, and low stability of ionic liquid. CN102701923A describe a cannula reactor equipped with recirculated cooler, which aims at improving controlling of reactor temperature, but still fails to overcome drawbacks including undermixing of reactants, nonuniform dispersion of catalyst, low conversion of reactants, high cost of trioxane and ionic liquid, and low stability of ionic liquid.

In conclusion, there is need for developing a new reactor for industrialized production of polyoxymethylene dimethyl ethers and relevant processes. Therefore, development of a reactor with low liquid back mixing, high conversion of reactants, high heat exchange capacity and high reaction efficiency is of great importance for industry application.

SUMMARY OF THE INVENTION

It is an object of the invention to design a novel reactor and method to overcome the above drawbacks. The object is achieved by a fluidized bed reactor and method for preparation of polyoxymethylene dimethyl ethers from dimethoxymethane and paraformaldehyde.

The fluidized bed reactor for preparation of polyoxymethylene dimethyl ethers from dimethoxymethane and paraformaldehyde, could be single- or multi-stage, and equipped with a bottom component. When the reactor is a multi-stage fluidized bed reactor, one or more interstage components are installed inside the reactor above the bottom component, thus dividing the space between the bottom component and the top of the reactor into two or more stages fluidized bed reactor.

In each stage of the fluidized bed reactor, a catalyst inlet is installed at upper region of the reactor wall and a catalyst outlet is installed at lower region of the reactor wall. Besides, a gas distributor is installed near the bottom of the stage.

The gas distributor in the lowest stage is connected with a gas inlet disposed at bottom of the reactor wall through a bottom component related gas upward channel. The bottom component related gas upward channel is disposed through the bottom component. The gas distributors in stages above the lowest stage are connected with an adjacent lower stage through an interstage component related gas upward channel. The interstage component related gas upward channel (212, 312-1, 312-2) is passed through the interstage component An inlet channel of fluid is disposed on the top stage of the reactor, and inserted through the top of the fluidized bed reactor, with one end outside the top stage and the other end inside the top stage. A bottom downcomer is disposed in the lowest stage and is disposed through the bottom component. Both ends of the bottom downcomer are located inside the fluidized bed reactor, with one end above the bottom component and the other end below the bottom component. An interstage downcomer is installed across two adjacent stages and is disposed through corresponding interstage component.

A fluid outlet is settled at the bottom of the fluidized bed reactor. A gas outlet is settled at the top shell of the top stage of the fluidized bed reactor.

A strain is disposed at an inlet of the bottom downcomer, and/or an inlet of the interstage downcomer to prevent solid catalyst or solid paraformaldehyde from entering into space below the bottom component or into an adjacent lower stage of the fluidized reactor.

The gas distributor could be a plate-type distributor or a tubular distributor. When the gas distributor is a plate-type distributor, multiple pores or multiple nozzles are provided on the plate-type distributor. When the gas distributor is a tubular distributor, the tubular distributor is of ring type, with 1~5 rings and multiple pores or multiple nozzles are set on each ring.

The cross section area of the bottom component related gas upward channel is 0.1%~20% of the cross section area of the bottom component.

The cross section area of the interstage component related gas upward channel is 0.1%~20% of the cross section area of the interstage component.

A method for preparation of polyoxymethlene dimethyl ethers from dimethoxymethane and paraformaldehyde by use of the above mentioned fluidized bed reactor is proposed, comprising the steps of:

a. When the fluidized bed reactor is a single-stage fluidized bed reactor, the fluidizing gas flows into the reactor through the gas inlet, then enters bed through the bottom component related gas upward channel via the gas distributor. The fluidizing gas goes upwards and flows out of the reactor via the gas outlet. Paraformaldehyde and dimethoxymethane flow into the reactor through the fluid inlet. The fluid goes downwards after the fluid level reaches the inlet of the downcomer and finally leaves the fluidized bed reactor via the fluid outlet at bottom of the reactor.

b. When the fluidized bed reactor is a multi-stage fluidized bed reactor, the fluidizing gas flows into the reactor through the gas inlet, and then enters the bottom stage fluidized bed through the bottom component related gas upward channel via the corresponding gas distributor. The fluidizing gas flows upward into a higher and next stage fluidized bed via the interstage component related gas upward channel, successively and finally leaves the top stage fluidized bed via the gas outlet. Paraformaldehyde and dimethoxymethane, after being mixed, flow into the top stage fluidized bed through the fluid inlet. The fluid flows downwards into a lower and next stage fluidized bed through the corresponding downcomer successively, and finally leaves the reactor via the fluid outlet.

According to a preferred embodiment, a jacketed heat exchanger for temperature control is installed at outside of the fluidized bed reactor wall and is connected therewith. The heat transferring medium adopted by the jacketed means for temperature control could be one or more of hot water, steam, thermal oil and cooling water.

According to a preferred embodiment, material of the fluidized bed reactor could be carbon steel or stainless steel.

According to a preferred embodiment, the temperature of each stage fluidized bed could be in the range of 40° C.~120° C.

According to a preferred embodiment, the operation pressure of each stage fluidized bed could be in the range of 0~0.5 MPa (absolute pressure).

The advantageous effects of this invention including:

The fluidized bed reactor for preparation of polyoxymethylene dimethyl ethers from dimethoxymethane and paraformaldehyde could realize the break through from previous lab-scale study to large-scale industrialized production of polyoxymethylene dimethyl ethers.

In the fluidized bed reactor for preparation of polyoxyethylene dimethyl ethers from dimethoxymethane and paraformaldehyde, the fluidizing gas flows up while the fluid flows down. This countercurrent flow could enhance the reaction driving force and improve the product size distribution. Countercurrent flow is hard to realize using traditional fixed bed reactor, thus losing the above advantages.

In the fluidized bed reactor for preparation of polyoxyethylene dimethyl ethers from dimethoxymethane and paraformaldehyde, the downcomer for fluid downing to lower stage fluidized bed make countercurrent flow easier to be realized, thus further enhancing the reaction driving force and improving the product size distribution.

In the fluidized bed reactor for preparation of polyoxyethylene dimethyl ethers from dimethoxymethane and paraformaldehyde, the strainer installed at the inlet of downcomer could effectively avoid solid catalyst or paraformaldehyde downing to lower stage fluidized reactor or space. This design could avoid catalyst leaching and maintain the optimum catalyst loading level, thus keeping the reactor stable.

For the fluidized bed reactor for preparation of polyoxyethylene dimethyl ethers from dimethoxymethane and paraformaldehyde, solid acid is the optimum catalyst. Compared with ionic liquid used in previous technologies, solid acid has advantages including low cost, easy recycling, easy separation and simple process.

Compared with a conventional cannula reactor, the fluidized bed reactor is in favor of improving dispersion uniformity of catalyst and conversion of formaldehyde.

BRIEF DESCRIPTION OF THE DRAWINGS

FIG. 1 is a structure diagram of a single-stage fluidized bed. 101—gas inlet; 102—gas distributor; 103—catalyst inlet; 104—fluid inlet; 105—gas outlet; 106—downcomer; 107—bottom component; 108—catalyst outlet; 109—bottom component related gas upward channel; 110—fluid outlet.

FIG. 2 is a structure diagram of a two-stage fluidized bed. 201—gas inlet; 202-1, 202-2—gas distributor; 203-1,203-2—catalyst inlet; 204—fluid inlet; 205—gas outlet; 206-1—bottom downcomer; 206-2—interstage downcomer; 207—bottom component; 208-1, 208-2—catalyst outlet; 209—bottom component related gas upward channel; 210—fluid outlet; 211—interstage component; 212—interstage component related gas upward channel.

FIG. 3. is a structure diagram of a three-stage fluidized bed. 301—gas inlet; 302-1, 302-2, 302-3—gas distributor; 303-1,303-2,303-3—catalyst inlet; 304—fluid inlet; 305—gas outlet; 306-1—bottom downcomer; 306-2, 306-3—interstage downcomer; 307—bottom component; 308-1, 308-2, 308-3—catalyst outlet; 309—bottom component related gas upward channel; 310—fluid outlet; 311-1, 311-2—interstage component; 312-1, 312-2—interstage component related gas upward channel.

DETAILED DESCRIPTION OF EMBODIMENTS

Term "bed" refers to each stage fluidized bed filled with catalyst, in case of a multiple stage fluidized bed, each stage has corresponding bed, and "bottom bed" refers to the stage bed located at the bottom of the fluidized bed reactor.

Term "bottom component" means the component at the bottom inside the fluidized bed. Term "interstage component" refers to a component set between two adjacent beds for separating a whole fluidized bed reactor into multiple stage fluidized beds. The bottom component or interstage component is used for separation of adjacent beds and keep each stage fluidized bed independent.

Paraformaldehyde is mixture of linear chain polymers of formaldehyde with a polymerization degree in the range of 8-100. Compared with trioxane, paraformaldehyde has lower solubility in dimethoxymethane, but saves the cost by about 50%.

Figure 1:
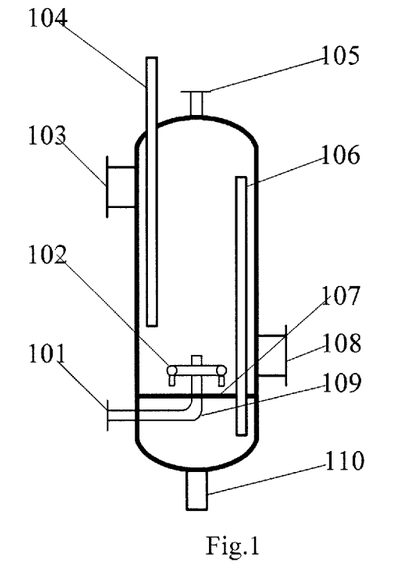
Figure 2:
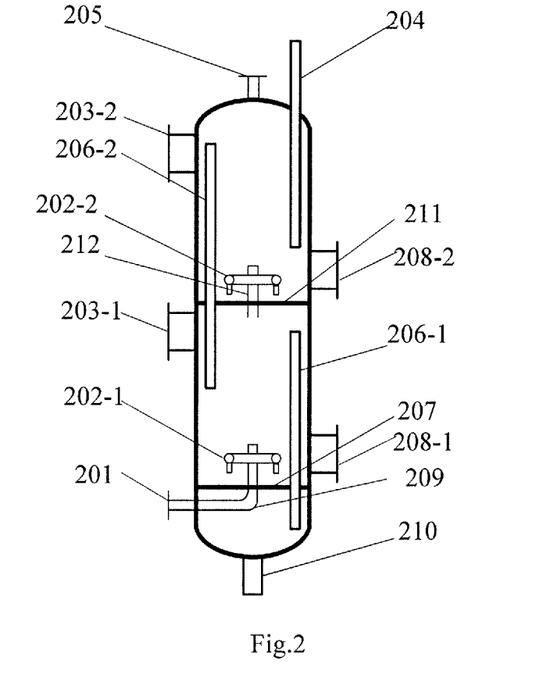
Figure 3:
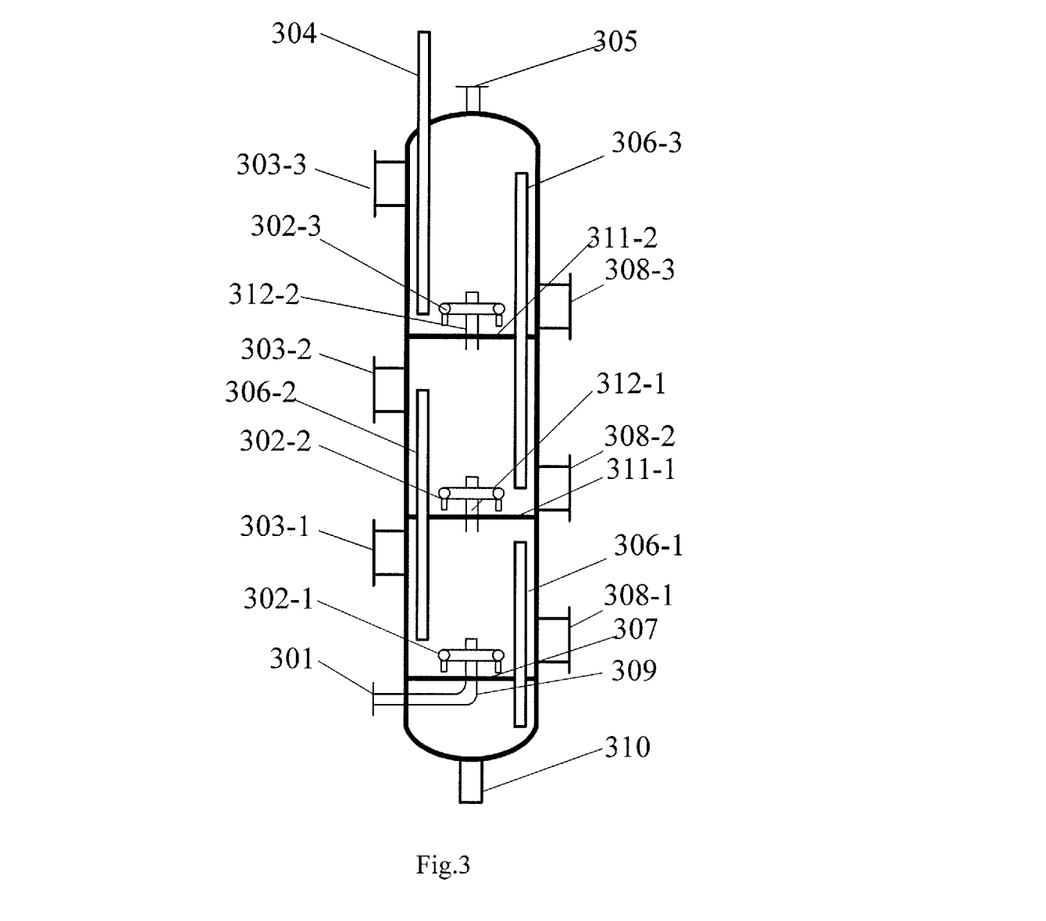

In one embodiment, there is provided a fluidized bed reactor for preparation of polyoxymethylene dimethyl ethers from dimethoxymethane and paraformaldehyde. The fluidized bed reactor could be single-stage or multi-stage, and equipped with a bottom component 107, 207 and 307 for separation. In one example, the fluidized bed reactor is a multi-stage fluidized bed reactor, and one or more interstage components 211, 311-1 and 311-2 are installed inside the reactor and above the bottom component 107, 207 and 307, thus dividing the space between the bottom component and the top of the reactor into two or more stages.

In each stage of the fluidized bed reactor, a catalyst inlet 103, 203-1, 203-2, 303-1, 303-2 or 303-3 is installed at upper region of a reactor wall corresponding to the stage and a catalyst outlet 108, 208-1, 208-2, 308-1, 308-2 or 308-3 is installed at lower region of the reactor wall. Besides, a gas distributor 102, 202-1, 202-2, 302-1, 302-2 or 302-3 is disposed near the bottom of each stage fluidized bed.

The gas distributor 102, 202-1 or 302-1 in the lowest stage is connected with a gas inlet 101, 201 or 301. The gas inlet 101, 201 or 301 is disposed at bottom of the reactor wall through a bottom component related gas upward channel 109, 209 or 309. The bottom component related gas upward channel 109, 209 or 309 is disposed through the bottom component 107, 207 or 307. The gas distributors 202-2, 302-2 or 302-3 in the upper stages (that is, stages above the lowest stage) are connected with the adjacent lower stage through an interstage component related gas upward channel 212, 312-1 or 312-2. The interstage component related gas upward channel (212, 312-1, 312-2) is passed through the corresponding interstage component 211, 311-1 or 311-2.

An inlet channel of fluid 104, 204 or 304 is disposed on the top stage of the reactor, and inserted through the top of the fluidized bed reactor, with one end located outside the top stage, and the other end inside the top stage. A bottom downcomer 106, 206-1 or 306-1 is disposed in the lowest stage and is disposed through the bottom component 107, 207 or 307, both ends of the bottom downcomer are located inside the fluidized bed reactor, with one end above the bottom component and the other end below the bottom component. An interstage downcomer 206-2, 306-2 or 306-3 is installed across two adjacent stages and is disposed through corresponding interstage component 211, 311-1 or 311-2.

An fluid outlet 110, 210 or 310 is disposed at the bottom of the fluidized bed reactor. An gas outlet 105, 205 or 305 is disposed at the top shell of the top stage of the fluidized bed reactor.

In one embodiment, a strain is mounted at an inlet of the bottom downcomer 106, 206-1, 306-1 and/or an inlet of the interstage downcomer 206-2, 306-3 or 306-3, to prevent solid catalyst or solid paraformaldehyde from entering into an adjacent lower stage fluidized reactor or into space below the bottom component 107,207 or 307 or into an adjacent lower stage of the fluidized reactor.

The gas distributor 102, 202-1, 202-2, 302-1, 302-2 or 302-3 could be a plate-type distributor or a tubular distributor. In case of plate type, multiple pores or nozzles can be arranged or provided on the distributor. In case of tubular type, the tubular distributor can be of ring type, and can have 1~5 rings, with multiple pores or nozzles arranged on each ring.

In one embodiment, the cross section area of the bottom component related gas upward channel 109, 209 or 309 can be 0.1%~20% of the cross section area of the bottom component.

The cross section area of the interstage component related gas upward channel 212, 312-1 or 312-2 is 0.1%~20% of the cross section area of the interstage component 211, 311-1 or 311-2.

Example 1

In this example, the fluidized bed reactor is a single-stage bed, as shown in FIG. 1.

The single-stage fluidized bed reactor comprises: a fluid inlet 104 and a gas outlet 105 disposed at upper region of the reactor wall; a catalyst inlet 103 disposed at upper region of the reactor wall; a catalyst outlet 108 disposed at lower region of the reactor wall; a gas inlet 101 and a fluid outlet 110 disposed at the bottom of the reactor; a bottom component 107 disposed at bottom of bed and inside the bed; a bottom component related gas upward channel 109 and a downcomer 106 disposed through the bottom component 107; a gas distributor 102 connected with the bottom component related gas upward channel 109. The gas distributor can be connected with the bottom component through the bottom component related gas upward channel 109.

In this example, the gas distributor 102 could be a tubular distributor in ring type, with 1~5 rings, preferably 2~3 rings, and a plurality of pores or nozzles are arranged on each ring. The cross section area of the bottom component related gas upward channel 109 is 0.1%~20%, preferably 0.1~5% or more preferably 3~4%, of the cross section area of the bottom component 107. The gas distributor 102 could also be a plate-type distributor, which can be directly formed via punching on the bottom component. The area of pores on the bottom component 107 can be 0.1%~20%, preferably 0.1~5% or more preferably 3~4%, of the cross section area of the component.

Material of the fluidized bed reactor could be carbon steel or stainless steel.

In one example, the process for preparation of polyoxymethylene dimethyl ethers from dimethoxymethane and paraformaldehyde can comprise the following steps.

Solid acid catalyst is loaded into the fluidized bed reactor via the catalyst inlet 103. The solid concentration could be 5%~40%, preferably 5%~20% or more preferably 10%~15%. Deactivated catalyst is discharged through the catalyst outlet 108. Both the catalyst inlet 103 and the catalyst outlet 108 are installed on the reactor wall. In this example, the catalyst is solid acid, such as molecular sieves, ion exchange resin and et al. Paraformaldehyde and dimethoxymethane flow into the fluidized bed reactor through the fluid inlet 104. It is preferable to mix paraformaldehyde and dimethoxymethane before entering them into the fluid inlet 104, to facilitate solid transport. The fluid goes downwards into the space under the bottom component 107 through the bottom downcomer 106 after the fluid level reaches the inlet of the downcomer 106. Finally, the fluid leaves the fluidized bed reactor via the fluid outlet 110 at bottom of the reactor. The fluidizing gas flows into the reactor through the gas inlet 101, then enters the bed through the bottom component related gas upward channel 109, which is disposed through the bottom component 107 and is connected with gas distributor 102.

In one preferable embodiment, inert gas is used as the fluidizing gas.

In another preferable embodiment, superheated steam of dimethoxymethane is used as the fluidizing gas, thus dimethoxymethane works both as the fluidizing gas and as a reactant simultaneously. This could significantly decrease amount of by-products and improve conversion of formaldehyde.

The fluidizing gas flows into the bed and fluidifying the bed, thus making the catalyst uniformly dispersed in the bed. The fluidizing gas goes upward and flows out the reactor via the gas outlet 105. The operation temperature could be 40~120° C., preferably 80~100° C. and more preferably 85~95° C. Too high temperature would cause deactivation of the catalyst, while too low temperature would decrease the reaction rate. The operation pressure could be in the range of 0~0.5 MPa (absolute pressure).

A jacketed heat exchanger for temperature control can be installed at outside of the fluidized bed reactor wall. The heat transferring medium could be one or more of hot water, steam, thermal oil and cooling water.

The fluidized bed reactor for preparation of polyoxymethylene dimethyl ethers from dimethoxymethane and paraformaldehyde according to the embodiment could realize the break through from previous lab-scale study to large-scale industrialized production of polyoxymethylene dimethyl ethers.

In the fluidized bed reactor for preparation of polyoxymethylene dimethyl ethers from dimethoxymethane and paraformaldehyde according to the embodiment, the fluidizing gas flows upwards while the fluid (which is liquid and may comprise reactants and products) flows downwards. This countercurrent flow could enhance the reaction driving force and improve the product size distribution. It is difficult for traditional fixed be reactor to realize such countercurrent flow.

In the fluidized bed reactor for preparation of polyoxymethylene dimethyl ethers from dimethoxymethane and paraformaldehyde according to the embodiment, a downcomer is disposed for directing fluid bed level of which is above the inlet of the downcomer flowing downwards into the space below the bottom component, so as to make countercurrent flow easier to be realized, and further enhance reaction driving force and improve product size distribution.

In the fluidized bed reactor for preparation of polyoxymethylene dimethyl ethers from dimethoxymethane and paraformaldehyde according to the embodiment, the strainer installed at the inlet of downcomer could effectively prevent solid catalyst or paraformaldehyde from entering into lower stage fluidized reactor or space below the bottom component. This design could avoid catalyst leaching and maintain the optimum catalyst loading level, thus keep the reactor stable.

For the fluidized bed reactor for preparation of polyoxymethylene dimethyl ethers from dimethoxymethane and paraformaldehyde according to the embodiment, solid acid is a preferable catalyst. Compared with ionic liquid commonly used in previous technologies, solid acid in this example has advantages including low cost, easy recycling, easy separation and simple process.

Compared with a traditional cannula reactor, the fluidized bed reactor in this example facilitates dispersion uniformity of catalyst and conversion of formaldehyde.

Example 2

In this example, the fluidized bed reactor is a two-stage bed, as shown in FIG. 2.

The two-stage fluidized bed reactor comprises: a bed body; a fluid inlet 204 and a gas outlet 205 installed on the top of the reactor; a catalyst inlet 203-1, 203-2 installed at upper region of each stage reactor wall; a catalyst outlet 208-1, 208-2 installed at lower region of each stage reactor wall; a gas inlet 201 and a fluid outlet 210 settled at bottom of the reactor; a bottom component 207 disposed at bottom of the reactor and inside the lowest stage bed; a bottom component related gas upward channel 209 and a bottom downcomer 206-1 disposed through the bottom component 207; a gas distributor 202-1 connected with the bottom component related gas upward channel 209 in the regard of gas flow; an interstage component 211 installed above the bottom component 207 and inside the fluidized bed reactor; an interstage component related gas upward channel 212 and an interstage downcomer 206-2 disposed through the interstage component 211, a gas distributor 202-2 connected with the interstage component related gas upward channel 212.

In this example, the gas distributor 202-1, 202-2 could be a tubular distributor in ring type, with 1~5 rings, preferably 2~3 rings, and a plurality of pores or nozzles are arranged on each ring. The cross section area of the bottom component related gas upward channel 209 is 0.1%~20%, preferably 0.1~5% and preferably 3~4%, of the cross section area of the bottom component. The cross section area of the interstage component related gas upward channel 212 is 0.1%~20%, preferably 0.1~5%, and more preferably 3~4%, of the cross section area of the interstage component. The gas distributor 202-1, 202-2 could also be a plate-type distributor, which can be directly formed via punching on the bottom component.

In one example, the process for preparation of polyoxymethlene dimethyl ethers from dimethoxymethane and paraformaldehyde using the two-stage fluidized bed can comprise the following steps.

Solid acid catalyst is loaded into each stage fluidized bed via catalyst inlets 203-1 and 203-2. The solid concentration could be 5%~40%, preferably 5%~20%, and more preferably 10%~15%.

Paraformaldehyde and dimethoxymethane flow into the top stage fluidized bed through the fluid inlet 204. In this example, it is preferable to mix paraformaldehyde and dimethoxymethane before entering them into the fluid inlet 204, to facilitate solid transport.

In the top stage bed, after the fluid level reaches the inlet of the downcomer 206-2, the fluid goes downwards to the bottom stage bed through the interstage downcomer 206-2. In the bottom stage bed, after the fluid level reaches the inlet of the bottom downcomer 206-1, the fluid goes downwards to the space below the bottom component 207 through the downcomer 206-1. Finally, the fluid leaves the fluidized bed reactor via the fluid outlet 210 at bottom of the reactor.

Fluidizing gas flows into the reactor through the gas inlet 201, then enters the bottom stage fluidized bed through the bottom component related gas upward channel 209 via gas distributor 202-1.

In this example, it is preferably using inert gas as the fluidizing gas.

In another example, it is preferably using superheated steam of dimethoxymethane as the fluidizing gas. Herein, dimethoxymethane works as the fluidizing gas and a reactant simultaneously. This could significantly decrease amount of by-products and improve conversion of formaldehyde.

The fluidizing gas flows into the bottom stage bed and fluidifying the bed, thus making the catalyst uniformly dispersed in the bottom stage bed. Thereafter, the fluidizing gas goes upwards to the top stage bed through the interstage component related gas upward channel 212 and fluidifying the bed, thus making the catalyst uniformly dispersed in the top stage bed. Finally, the fluidizing gas flows out of the reactor via the gas outlet 205. The operation temperature could be 40~120° C., preferably 80~100° C. and more preferably 85~95° C. Too high temperature would cause deactivation of the catalyst, while too low temperature would decrease the reaction rate. The operation pressure could be in the range of 0~0.5 MPa (absolute pressure).

The two-stage fluidized bed reactor in this example has all the above-mentioned advantages that the single-stage fluidized bed reactor has. Besides, the two-stage fluidized bed reactor gives higher per-pass conversion of formaldehyde than the single-stage fluidized bed reactor.

Example 3

In this example, the fluidized bed reactor is a three-stage bed, as shown in FIG. 3. The three-stage bed consists of a top stage fluidized bed, a middle stage fluidized bed and a bottom stage fluidized bed. The three-stage fluidized bed reactor comprises: a bed body, a fluid inlet 304 and a gas outlet 305 installed on the top of the reactor; catalyst inlets 303-1, 303-2 and 303-3 installed at upper region of each stage reactor wall; catalyst catalyst outlets 308-1, 308-2 and 308-3 installed at lower region of each stage reactor wall; a gas inlet 301 and a fluid outlet 310 settled at bottom of the reactor; a bottom component 307 disposed inside the lowest stage bed and at the bottom of the reactor; a bottom component related gas upward channel 309 and a bottom downcomer 306-1 disposed through the bottom component 307; a gas distributor 302-1 connected with the bottom component related gas upward channel 309 in the regard of gas flow; interstage components 311-1 and 311-2 installed above the bottom component 307 and inside the fluidized bed reactor; interstage component related gas upward channels 312-1 and 312-2 and interstage downcomers 306-2 and 306-3 disposed through the interstage components 311-1 and 311-2; and gas distributors 302-2 and 302-3 connected with the interstage component related gas upward channel 312-1, 312-2 respectively.

In this example, the gas distributors 302-1, 202-2 and 302-3 could be a tubular distributor in ring type, with 1~5 rings, preferably 2~3 rings, and a plurality of pores or nozzles are arranged on each ring. The cross section area of the bottom component related gas upward channel 309 is 0.1%~20%, preferably 0.1%~5% and more preferably 3~4%, of the cross section area of the bottom component. The cross section area of the interstage component related gas upward channel 312-1 or 312-2 is 0.1%~20%, preferably 0.1%~5%, and more preferably 3~4%, of the cross section area of the corresponding interstage component. Each of the gas distributors 302-1, 202-2 and 302-3 could also be a plate-type distributor, which can be directly formed via punching on the bottom component. The area of the pores on each of the components 307, 311-1 and 311-2 is 0.1%~20%, preferably 0.1~5%, and more preferably 3~4%, of the cross section area of the corresponding component.

Material of the fluidized bed reactor could be carbon steel or stainless steel.

A jacketed heat exchanger is installed at outside of the fluidized bed reactor wall. The heat transferring medium could be one or more of hot water, steam, thermal oil and cooling water.

In one example, the process for preparation of polyoxymethylene dimethyl ethers from dimethoxymethane and paraformaldehyde using the three-stage fluidized bed can comprise the following steps.

Solid acid catalyst is loaded into each stage fluidized bed via each of catalyst inlets 303-1, 303-2 and 303-3. The solid concentration could be 5%~40%, preferably 5%~20%, and more preferably 10%~15%. The deactivated catalyst is discharged through catalyst outlet 308-1, 308-2 and 308-3. Both catalyst inlets 303-1, 303-2 and 303-3 and catalyst outlets 308-1, 308-2 and 308-3 are installed on the reactor wall. In this example, the catalyst is preferably solid acid, such as molecular sieves, ion exchange resin and the like.

Paraformaldehyde and dimethoxymethane flow into the top stage fluidized bed through the fluid inlet 304. In this example, to facilitate solid transferring, it is preferable to mix paraformaldehyde and dimethoxymethane before entering them into the fluid inlet 304. In the top stage bed, the fluid goes downwards to the middle stage bed through the interstage downcomer 306-3 after the fluid level reaches the inlet of the interstage downcomer 306-3. In the middle stage bed, the fluid goes downwards to the bottom stage bed through the interstage downcomer 306-2 after the fluid level reaches the inlet of the interstage downcomer 306-2. In the bottom stage bed, the fluid goes downwards to the space under the bottom component 307 through the bottom downcomer 306-1 after the fluid level reaches the inlet of the bottom downcomer 306-1. Finally, the fluid leaves the fluidized bed reactor via the fluid outlet 310 at bottom of the reactor.

Fluidizing gas flows into the reactor through the gas inlet 301, and then enters bottom stage bed through the bottom component related gas upward channel 309 via gas distributor 302-1. The fluidizing gas flows into the bottom stage bed and fluidifying the bottom stage bed, thus making the catalyst uniformly dispersed in the bottom stage bed. The gas goes upwards to the middle stage bed through the interstage component related gas upward channel 312-1 and fluidifying the middle stage bed, thus making the catalyst uniformly dispersed in the middle stage bed. Then, the fluidizing gas goes upwards to the top stage bed through the interstage component related gas upward channel 312-2 and fluidifying the top stage bed, thus making the catalyst uniformly dispersed in the middle stage bed. Finally, the fluidizing gas flows out the reactor via the gas outlet 305. The operation temperature could be 40~420° C., preferably 80~100° C., and more preferably 85~95° C. Too high temperature would cause deactivation of the catalyst, while too low temperature would decrease the reaction rate. The operation pressure could be in the range of 0~0.5 MPa (absolute pressure).

The three-stage fluidized bed reactor in this example has all the advantages that the two-stage fluidized bed reactor shows. Besides, the three-stage fluidized bed reactor gives higher per-pass conversion of formaldehyde than the two-stage fluidized bed reactor.

The above examples describe single-stage, two-stage and three-stage fluidized bed reactor and method for preparation of polyoxymethylene dimethyl ethers from dimethoxymethane and paraformaldehyde. However, the reactor could consist of more stages. It should be noted that the per-pass conversion of reactants could be enhanced as the number of stage increases. However, the structure of reactor would be more complicated, and the cost would increase. The number of stage should be chosen according to actual demand.

What is claimed is:

1. A fluidized bed reactor for preparation of polyoxymethylene dimethyl ethers from dimethoxymethane and paraformaldehyde,
   wherein the reactor is single-stage or multi-stage, and equipped with a bottom component (107, 207, 307); when the reactor is a multi-stage fluidized bed reactor, one or more interstage components (211, 311-1, 311-2) are installed inside the reactor above the bottom component (107, 207, 307), thus dividing the space between the bottom component (107, 207, 307) and the top of the reactor into two or more stages;
   in each stage of the fluidized bed reactor, a catalyst inlet (103, 203-1, 203-2, 303-1, 303-2, 303-3) is disposed at upper region of the reactor wall, a catalyst outlet (108, 208-1, 208-2, 308-1, 308-2, 308-3) is disposed at lower region of the reactor wall; and a gas distributor (102, 202-1, 202-2, 302-1, 302-2, 302-3) is installed near bottom of the stage;
   the gas distributor (102, 202-1, 302-1) in the lowest stage is connected with a gas inlet (101, 201, 301) disposed at bottom of the reactor wall through a bottom component related gas upward channel (109, 209, 309); the bottom component related gas upward channel (109, 209, 309) is disposed through the bottom component (107, 207, 307); the gas distributors (202-2, 302-2, 302-3) in stages above the lowest stage are connected with an adjacent lower stage through an interstage component related gas upward channel (212, 312-1, 312-2); the interstage component related gas upward channel (212, 312-1, 312-2) is passed through the interstage component (211, 311-1, 311-2);
   an inlet channel of fluid (104, 204, 304) is disposed on the top stage of the reactor, and inserted through the top of the fluidized bed reactor, with one end outside the top stage and the other end inside the top stage; a bottom downcomer (106, 206-1, 306-1) is disposed in the lowest stage and is disposed through the bottom component (107, 207, 307), both ends of the bottom downcomer are located inside the fluidized bed reactor, with one end above the bottom component and the other end below the bottom component; an interstage downcomer (206-2, 306-2, 306-3) is installed across two adjacent stages and is disposed through corresponding interstage component (211, 311-1, 311-2);
   a fluid outlet (110, 210, 310) is disposed at the bottom of the fluidized bed reactor, a gas outlet (105, 205, 305) is disposed at the top wall of the top stage of the fluidized bed reactor.

2. The fluidized bed reactor for preparation of polyoxymethylene dimethyl ethers from dimethoxymethane and paraformaldehyde according to claim 1, wherein a strain is installed at an inlet of the bottom downcomer (106, 206-1, 306-1) and/or an inlet of the interstage downcomer (206-2, 306-2, 306-3), to prevent solid catalyst or solid paraformaldehyde from entering into space below the bottom component (107, 207, 307) or into an adjacent lower stage of the fluidized reactor.

3. The fluidized bed reactor for preparation of polyoxymethylene dimethyl ethers from dimethoxymethane and paraformaldehyde according to claim 1, wherein the gas distributor (102, 202-1, 202-2, 302-1, 302-2, 302-3) is a plate-type distributor, and multiple pores or multiple nozzles are provided on the plate-type distributor.

4. The fluidized bed reactor for preparation of polyoxymethylene dimethyl ethers from dimethoxymethane and paraformaldehyde according to claim 1, wherein the gas distributor (102, 202-1, 202-2, 302-1, 302-2, 302-3) is a tubular distributor.

5. The fluidized bed reactor for preparation of polyoxymethylene dimethyl ethers from dimethoxymethane and paraformaldehyde according to claim 4, wherein the tubular distributor is of ring type, with 1~5 rings and multiple pores or multiple nozzles are set on each ring.

6. The fluidized bed reactor for preparation of polyoxymethylene dimethyl ethers from dimethoxymethane and paraformaldehyde according to claim 1, wherein cross section area of the bottom component related gas upward channel (109, 209, 309) is 0.1%~20% of cross section area of the bottom component.

7. The fluidized bed reactor for preparation of polyoxymethylene dimethyl ethers from dimethoxymethane and paraformaldehyde according to claim 1, wherein the cross section area of the interstage component related gas upward channel (212, 312-1, 312-2) is 0.1%~20% of the cross section area of the interstage component.

8. A method for preparation of polyoxymethylene dimethyl ethers from dimethoxymethane and paraformaldehyde by use of the fluidized bed reactor according to claim 1, comprising steps of:
   a. when the fluidized bed reactor is a single-stage fluidized bed reactor, the fluidizing gas flows into the reactor through the gas inlet (101), then enters bed through the bottom component related gas upward channel (109) via the gas distributor (102); the fluidizing gas goes upward and flows out of the reactor via the gas outlet (105); paraformaldehyde and dimethoxymethane flow into the reactor through the fluid inlet (104), and the fluid goes downwards through the downcomer (106) after the fluid level reaches the inlet of the downcomer (106), and finally leaves the fluidized bed reactor via the fluid outlet (110) at bottom of the reactor,
   b. when the fluidized bed reactor is a multi-stage fluidized bed reactor, the fluidizing gas flows into the reactor through the gas inlet (201, 301), then enters the bottom stage fluidized bed through the bottom component related gas upward channel (209, 309) via the corresponding gas distributor (202-1, 302-1); the fluidizing gas flows upward into a higher and next stage fluidized bed via the interstage component related gas upward channel (212, 312-1, 312-2) successively, and at last leaves the top stage fluidized bed via the gas outlet (205, 305); paraformaldehyde and dimethoxymethane, flow into the top stage fluidized bed through the fluid inlet (204, 304); the fluid flows downwards into a lower and next stage fluidized bed through the corresponding downcomer (206-1, 306-1; 206-2, 306-2, 306-3) successively, and at last leaves the reactor via the fluid outlet (210, 310).

9. The method for preparation of polyoxymethylene dimethyl ethers from dimethoxymethane and paraformaldehyde according to claim 8, wherein a jacketed means for temperature control is installed at outside of the fluidized bed reactor wall.

10. The method for preparation of polyoxymethylene dimethyl ethers from dimethoxymethane and paraformaldehyde according to claim 9, wherein heat transferring medium adopted by the jacketed means for temperature control is one or more of hot water, steam, thermal oil and cooling water.

11. The method for preparation of polyoxymethylene dimethyl ethers from dimethoxymethane and paraformaldehyde according to claim 8, wherein the material of the fluidized bed reactor is carbon steel or stainless steel.

12. The method for preparation of polyoxymethylene dimethyl ethers from dimethoxymethane and paraformaldehyde according to claim 8, wherein the temperature of each stage fluidized bed is in the range of 40° C.~120° C.

13. The method for preparation of polyoxymethylene dimethyl ethers from dimethoxymethane and paraformaldehyde according to claim 8, wherein the operation pressure of each stage fluidized bed is in the range of 0~0.5 MPa.

* * * * *